United States Patent [19]

Webster

[11] Patent Number: 5,782,787
[45] Date of Patent: Jul. 21, 1998

[54] MOISTURE-RESPONSIVE ABSORBENT WOUND DRESSING

[75] Inventor: David Fitzgerald Webster, Percy, United Kingdom

[73] Assignee: Smith & Nephew plc, London, United Kingdom

[21] Appl. No.: 501,091
[22] PCT Filed: Feb. 14, 1994
[86] PCT No.: PCT/GB94/00291
  § 371 Date: Aug. 14, 1995
  § 102(e) Date: Aug. 14, 1995
[87] PCT Pub. No.: WO94/17765
  PCT Pub. Date: Aug. 18, 1995

[30] Foreign Application Priority Data

Feb. 15, 1993 [GB] United Kingdom ............ 9302970

[51] Int. Cl.⁶ ........................................ A61F 5/00
[52] U.S. Cl. ............... 602/46; 602/43; 602/56; 602/58
[58] Field of Search ............... 602/47, 46, 48, 602/52, 42, 904; 128/888, 889

[56] References Cited

U.S. PATENT DOCUMENTS

| | | |
|---|---|---|
| 2,896,618 | 7/1959 | Schaefer ........................ 602/47 |
| 5,277,954 | 1/1994 | Carpenter et al. ............. 428/71 |
| 5,328,450 | 7/1994 | Smith et al. .................. 602/46 X |
| 5,445,604 | 8/1995 | Lang ............................ 602/47 |

FOREIGN PATENT DOCUMENTS

| | | | |
|---|---|---|---|
| 0 122 085 | 10/1984 | European Pat. Off. . | |
| 0 171 268 | 2/1986 | European Pat. Off. . | |
| 0 190 814 | 8/1986 | European Pat. Off. . | |
| 190814 | 8/1986 | European Pat. Off. .......... | 602/54 |
| 2 093 702 | 9/1982 | United Kingdom . | |

Primary Examiner—Richard J. Apley
Assistant Examiner—Kim M. Lee
Attorney, Agent, or Firm—Larson & Taylor

[57] ABSTRACT

An absorbent wound dressing (1) includes a polymer foam layer (3) having a plurality of discrete zones (2) on at least one surface (4) of the foam layer, the material forming the zones being less swellable than the foam layer material, such that when the dressing is placed with the zones of polymeric material in contact with a wet surface, the zones move apart as the foam layer absorbs fluid and swells.

18 Claims, 2 Drawing Sheets

MOISTURE-RESPONSIVE ABSORBENT WOUND DRESSING

BACKGROUND OF THE INVENTION

The invention relates to a dressing useful in the treatment of lesions of the skin. More particularly this invention relates to a unitary dressing which is absorbent but which has a reduced tendency to adhere to the lesions of the skin.

It has been a recognized problem for a long time that dressings used on exuding lesions are inclined to suffer from either or both of the disadvantages that they sometimes tend to float away from a wound or else they sometimes tend to adhere to the wound surface.

The first of these disadvantages generally occurs when the wound is one that produces particularly large volumes of exudate. Normally the method of overcoming the problem is to provide the dressing with holes so that the exudate can pass through the holes to an absorbent and hence the dressing remains in contact with the wound. Certain attempts to achieve this end are disclosed in UK Patent Nos.778813, 1398011,1408345 and Application Nos.2061732 and 2074029. One successful dressing is MELOLIN (Trade Mark, available from Smith & Nephew, Hull. UK) which comprises a perforated synthetic polymer film and an absorbent cellulosic pad. The perforated film is placed next to the exuding wound, the exudate passes through the perforations and is absorbed in the pad. A more recent suggestion has been to use a perforated polytetrafluoroethylene film in an effort to minimize the risk of any adherency of the dressing to the wound.

The second of the above disadvantages usually occurs when the wound has dried out due to the lack of production of exudate. Attempts to remove the dressing will result in disturbance of the newly forming layer of the skin over the wound and hence wound healing is delayed. Generally the method of overcoming this problem is to provide the dressing with a continuous layer which retards the rate of loss of water. One effective means of achieving this end is described in British Patent No.1280631.

However, none of the known methods are free of disadvantages since what may be an excellent dressing for one kind of wound will be unsuitable for many other wounds since wounds differ greatly in their output of exudate. It has now been realized that, not only is there a need for a dressing which is suitable for use on a number of different wound types, there is also a need for a dressing which can better cope with the variation in rate of exudate production from a given wound.

SUMMARY OF THE INVENTION

A dressing now has been discovered which allows passage of a greater amount of exudate when in contact with an exudating wound. The new dressing has been found to have a further advantage in that it has properties which aid re-epithelialization of the wound.

Accordingly the present invention provides an absorbent dressing which comprises a conformable hydrophilic polymeric foam layer having a first surface and an opposed second surface, the first surface having a plurality of discrete zones of a polymeric material, the swellability on contact with water of the polymeric material being less than that of the polymer foam.

It has been found that when such a dressing is placed with the zones of polymeric material, in contact with a wet surface, the foam layer absorbs the fluid, eg. water or exudate and swells. The zones being discrete (ie. separated from one another) move apart, thereby increasing the surface area of the first surface of the foam available for absorption, thereby further aiding absorption. Movement apart of the zones on swelling of the foam layer, leads to the zones occupying an expanded position. As the water is absorbed, the amount of water available for absorption by the foam layer decreases. As the exudate passes across the first surface of the foam layer and enters into the foam layer, moisture vapour escapes across the second surface of the foam layer. As the moisture vapour escapes the foam dries and contracts. The contraction of the foam layer results in a reduction of the surface area of the first surface of the foam available for absorption. As the surface area of the first surface reduces, the zones move closer together, until they eventually return to a contracted position. As the zones move together the dressing becomes more occlusive.

DESCRIPTION OF PREFERRED EMBODIMENTS

When placed on a non-wet surface, the swelling of the foam layer does not occur. The zones though discrete, are close enough together to prevent drying out of a non-exuding wound. Most aptly the zones cover at least 70% of the surface area of the first surface of the foam layer. More favourably the zones cover at least 80% of the surface area and preferably the zones cover at least 90% of the surface area of the first surface of the foam layer. Normally not more than 99% of the surface area of the first surface of the foam layer will be covered and preferably not more than 95% of the surface area of the first surface of the foam layer will be covered, (% figures relate to the percentage of the surface area of the absorbent layer which has discrete zones, before absorption has occured, ie. the non-hydrated state).

By a wet surface is meant a surface upon which there is an aqueous liquid, for example water, blood, proteinaceous wound exudate or the like.

In one favored form, the second surface is covered by a moisture vapor permeable film. The presence of a moisture vapor permeable film aids as a control mechanism for the escape of moisture vapor from the absorbent layer.

In a more favored form the wound dressing is symmetrical and has discrete zones of polymer on both the first and second surfaces.

It is clear from the foregoing that dressings of the present invention are in a changing situation when placed in contact with a wet surface of an exuding wound. When zones are placed against the wound surface, exudate is absorbed by the first surface of the polymeric foam layer between the zones and the foam layer swells. Since the swellability on contact with water of the polymeric material is less than that of the synthetic polymeric foam, the zones move apart thereby exposing more of the first surface of the foam layer for absorption. Thus the more exudate is present the more the foam layer tends to swell and the more absorption takes place. As the amount of exudate present diminishes, the water vapor lost from the dressing by evaporation is greater than the absorption rate and the foam layer begins to contract, the zones moving back towards each other, until on a non-exuding wound they have regained or almost regained their original positions. When the zones are in the contracted position, they prevent the wound from drying out and therefore the dressing has a reduced tendency to adhere to the wound. If the dressing is placed on unbroken normal skin or a non-exuding wound this activity does not take place.

In a preferred embodiment, the second surface of the dressing has a plurality of discrete zones of the type described above, so that either the first or second surface may be placed against the wound so avoiding the risk of inadvertently applying the wrong side of the dressing to the wound. It will be appreciated that in use, the dressing of the present invention is placed on the wound such that the discrete zones contact the wound surface. Where the dressing comprises discrete zones on the first surface only of the foam layer, said first surface and discrete zones will form the wound-contacting layer of the dressing. The presence of discrete zones on the second surface will also tend to slow down the loss of water through the non-wound contacting side of the dressing, hence keeping the environment of the wound moist for longer but without affecting the absorption of exudate by the foam layer.

Whereas the zones may comprise a mixture, eg. a blend of different polymeric materials, it is preferred to use a single polymeric material. Preferably the polymeric material is a synthetic polymer. Less preferably the polymeric material is a natural polymer, eg. natural rubber latex. Similarly the foam layer may comprise a mixture of different materials. However it is preferred that the foam layer comprises a single material. The foam layer comprises a hydrophilic foam.

Suitably the foam layer comprises a conformable hydrophilic synthetic polymer which is adapted to be capable of absorbing the wound exudate. It is desirable that the foam layer absorbs the wound exudate rapidly as this enhances the effectiveness of this type of dressing. Suitable conformable hydrophilic foams will normally be flexible open cell foams.

The ability of open cell foams to absorb and retain fluids depends to some extent on the size of the foam cells and the porosity of the foam.

Suitable open cell hydrophilic foams have a cell size of 30 microns to 700 microns and preferably a cell size of 50 microns to 500 microns. Apt open cell foams have 20% to 70% and preferably 30% to 60% of the total membrane area of the cells as membrane openings. Such open cell foams when used in dressings of the present invention allow transport of fluid and cellular debris into and within the foam.

The hydrophilic polymeric foam may aptly be made from polyurethane, cellulose, carboxylated butadiene-styrene rubber, polyester foams, hydrophilic epoxy foams or polyacrylate. Such foams are hydrophilic per se. However they may also be treated to render them more hydrophilic, for example with surfactants. Use of foams comprising a hydrophilic polymer reduces the tendency for the exudate to coagulate rapidly in the foam. This helps to keep the wound in a moist condition even when production of exudate has ceased from the wound.

Favoured hydrophilic polymer foams are formed from hydrophilic polyurethane especially cross-linked hydrophilic polyurethane. Such hydrophilic polyurethanes will generally absorb at least 5% by weight of water when hydrated and aptly will absorb up to 300 or 400% of their weight of water when fully hydrated. Preferred foams include those described in EP-A-299122 and known as Hypol foams made from Hypol hydrophilic isocyanate terminated prepolymers (Hypol is a Trade Mark and is available from W R Grace and Co). The prepolymers are mixed with water and then cured.

The water absorption of the foam layer can fall within a wide range of water absorption as disclosed in EP0299122B, eg. in the range of 25–95% by weight of polymer. Preferably the water absorption is between 50 and 92% w/w.

Suitable hydrophilic foam absorbent layers have a thickness of 0.5 mm to 20 mm, more suitably 0.8 mm to 12 mm and preferably 1 mm to 8 mm, for example 4 mm to 6 mm.

Suitably the zones comprise a polymeric material, the swellability on contact with water of the polymeric material being less than that of the synthetic polymeric foam. Preferably the polymeric material does not swell in contact with water, ie. remains inert in the presence of fluid. Suitable polymers include polyurethane, polyvinyl chloride, polyethylene, polytetrafluorethylene, polybutadiene, polysilicones, polyester, silicones, vinylacetate polymers, polyamides, polyether-polyamides, polystyrene, styrene butadiene copolymers, styrene isoprene styrene copolymers, acrylates, cyanocrylates, polyvinyl acetate, phenolics and expoxy resins and the like. A preferred polymer is a polyurethane. Suitable polyurethanes include polyester and polyether polyurethanes, examples of which are the ESTANES (Registered Trade Mark of B F Goodrich Ltd). Suitable ESTANES include 5702, 5701 and 580201.

The abovementioned polymeric materials may be placed on the foam layer, using any suitable method for dispensing hot melt polymeric materials, eg. slot-die coating, gravure coating, roller coating, spraying, jetting and screen coating or printing.

The zones may project from the first and/or second surface to a degree consistent with operation of the dressing. The zones may broadly be subdivided into those which extend to a degree greater than the dimension of the main axis of the surface of the zone which contacts the wound hereinafter referred to as "projections" and those which extend to a degree less than the dimension of the main axis of the surface of the zone hereinafter referred to as "islands". For example, where the surface is disc-shaped, the dimension in question is the diameter.

Preferably the zones are discrete from one another, ie. they do not touch each other at their bases. Thus there is a space between each zone at its base, thus the zones form a pattern on the surface of the foam layer, the spaces defining the area of the foam layer free from zones.

The surface of the zones which contacts the wound, may have any shape. Preferably the surface is flat-topped rather than pointed. Aptly the surface is disc-shaped, oval, hemispherical or square shaped. The zones may be cubic, cylindrical, truncated pyramidal, hexagonal and the like. Preferably the zones are truncated pyramids and most preferably truncated square pyramids.

The degree of projection of the zones from the surface of the foam layer may be from 0.1 mm to 2.5 mm, more suitably 0.2 to 2.0 mm and preferably 0.5 to 2.0 mm.

Suitably there are from 2 to 15 zones $cm^{-1}$ and preferably 4 to 8 zones $cm^{-1}$, eg. 5, 6 or 7 zones per $cm^{-1}$.

Thus a favored arrangement of zones has a pattern of 5 zones $cm^{-1}$ in the form of a truncated square pyramid arranged in diagonal rows at 45° across the surface of the foam layer, the contacting surface, the zones being separated from neighboring zones by 0.4 mm. Preferably the zones slope at a conical angle of 60°.

A second favoured arrangement of zones has a pattern of 4 projections/$cm^{-1}$ in the form of truncated square pyramids arranged in diagonal rows at 45° across the dressing, the pyramids being 2 $mm^2$ at the base, 0.5 mm between base edges, sloping at a conical angle of 60° and 1.91 $mm^2$ at the wound-contacting surface.

As hereinbefore described the space between the bases of the zones allows wound exudate to come into contact with and be absorbed by the foam layer. The subsequent swelling, which leads to a linear expansion of the absorbent layer, increases the space between the bases of the zones. Typically the linear expansion is in the range of from 15 to 55%, more typically in the range of from 22 to 38%. After absorbing the exudate and upon drying of the dressing, the space between the bases of the zones returns substantially to its original value.

Normally the islands will be discrete from one another. The islands may touch along some distance of their perimeters but aptly there will be a space between each island for some distance of its perimeter. The islands may be of any shape. Aptly the islands will be circular, elliptical and the like. Preferably the islands will be square, rectangular, triangular, hexagonal or the like.

The thickness of the islands will be from 0.002 mm to 0.5 mm, more suitably 0.005 to 0.1 and preferably 0.01 to 0.5 mm.

Suitably the dressing of the invention will be adapted to have a moisture vapour permeability (MVP) in the range of from 200 to 5,000 $gm^{-2}$ 24 $hrs^{-1}$ at 37° C. at 100% to 10% relative humidity difference. The MVP can be measured according to the method disclosed for measuring the moisture vapour transmission rate in EP Application No.90905227.6. The dressing will aptly exhibit a lower permeability when on dry wounds (zones together) and will aptly exhibit a higher permeability on wet or highly exuding wounds (zones apart). It has been found that such moisture vapor permeabilities of the dressing allow the wound under the dressing to heal under moist conditions without causing the skin surrounding the wound to become macerated.

Where the second surface of the foam layer comprises a moisture vapor permeable film, said film may be continuous or discontinuous.

A preferred moisture vapor permeable film is a continuous, elastic, conformable film. The film aids in the regulation of water vapor loss from the wound area beneath the dressing. It also acts as a barrier to both bacteria and to liquid water.

Suitable moisture vapor permeable films are elastic, continuous, conformable films. Apt continuous films can have a MVP of greater than 300 $gm^{-2}$ $24h^{-1}$ at 37° C. and 100% to 10% relative humidity difference. Suitably the MVP will not normally be greater than 5000 $gm^{-2}$ $24h^{-1}$ at 37° C. and 100% to 10% relative humidity difference. Preferably, the MVP will be greater than 500, more preferably at least 700 and most preferably at least 2000 $gm^{-2}$ $24h^{-1}$ at 37° C. and 100% to 10% relative humidity difference.

Suitable polymers for use as a continuous film include polyether or polyester polyurethane or blends of polyurethanes with incompatible polymers such as polyolefins, for example polystyrene and may include those materials described above for producing the contoured apertured film. Aptly the films will be at least 12.5 μm thick. Suitable films will be up to 50 μm thick, favourably between 25 and 40 μm thick.

Preferred polyurethane films are made from linear polyurethanes. Favoured continuous films will be 12.5 μm to 37.5 μm thick. A preferred polyurethane for use in such thickness is ESTANE 5714F. A 25 μm thick film of ESTANE 5714F has a MVP of approximately 1800 gsm so that it may be employed to produce a moisture vapor transmission within the preferred range. Further suitable films include polyurethane or copolymers of alkoxy alkyl acrylates or methacrylates such as those disclosed in British Patent No.1280631.

The film may be a conformable polyurethane incompatible polymer blend films are disclosed in United Kingdom Patent Application No.2081721.

Alternatively a suitable conformable discontinuous moisture vapor permeable material may cover the second surface of the foam layer. Thus any moisture vapor permeable material normally used for wound dressings may be used. Such outer layers include conformable, elastic, porous and microporous films, non-woven fabrics, nets and woven and knitted fabrics.

Preferred discontinuous materials include extensible apertuerd non-woven fabrics and elastomer nets. Such preferred materials are disclosed in United Kingdom Patent Nos.2093702 and 2093703, which are incorporated herein by cross-reference.

An apt discontinuous material comprises a microporous film. Suitable conformable moisture vapor permeable microporous films have a permeability of 300 to 5000 $gm^{-2}$ $24hr^{-1}$ and preferably a permeability in the range of from 500 to 400 $gm^{-2}$ $24hr^{-1}$ at 37° C. at 100% relative humidity differences.

Suitable microporous films have a pore diameter of less than 2 μm, desirably less than 0.6 μm and preferably less than 0.1 μm. Suitably the pores will be larger than 0.01 μm.

Suitable polymers include plasticised polyvinyl chloride, polyurethane elastomers and ethylene-vinyl acetate copolymer elastomers. A favored conformable microporous film comprises a microporous plasticized polyvinyl chloride.

The conformable moisture vapor permeable film, non-woven fabric, net, woven or knitted fabric, which hereinafter will be referred by the generic term, backing layer, may comprise a moisture vapor permeable adhesive layer on a surface facing the foam layer, to bond the backing layer to the foam layer. Such an adhesive layer may be continuous or discontinuous.

Suitable adhesives which are moisture vapor permeable as a continuous layer including various acrylate ester copolymer and polyvinyl ethyl ether pressure sensitive adhesives, for example as disclosed in British Patent No.1280631. Favored pressure sensitive adhesives comprise copolymers of an acrylate ester with acrylic acid for example as disclosed in United Kingdom Application No.2070631A.

Suitable discontinuous adhesive layers for use on the backing layer may be any of those conventionally used for wound dressings. Such discontinuous adhesive layers can include porous, microporous or pattern spread layers.

Aptly the backing layer will be coextensive with the foam layer. Favourably the backing layer will have a greater surface area than the surface area of the second surface, so that the dressing can be adhered to the skin surrounding the wound. The backing layer being moisture vapour permeable, the skin beneath this part of the dressing, does not become macerated.

The dressings of the invention may contain a topically active medicament. Most suitably the medicament is an antibacterial agent. Preferably the antibacterial agent is a broad-spectrum antibacterial agent such as a silver salt, a sulphadiazine, an acceptable iodine source such as povidone iodine (also called polyvinyl pyrrolidone-iodine or PVP/I), chlorhexidine salts such as the gluconate, acetate, hydrochloride or the like salts or quaternary antibacterial agents such as benzalkonium chloride. Favored antibacterial agents include the salts of chlorhexidine. Preferably he medicament is present in the foam layer.

The dressing of this invention are most suitably sterile. Preferably the dressing is provided sealed within a bacteria-proof package. Such sterile dressings and such packages including the sterile dressing, thus form favored aspects of this invention. The dressing may be rendered sterile by any suitable sterilization means, for example by gamma irradiation, steam sterilisation or EtO.

One process of manufacturing the dressings of the present invention, is by casting the polymeric material into appropriately shaped recesses in a sheet material. A suitable material for forming the sheet is a silicone material which allows easy release of the zones from the sheet when desired. The polymeric material is usually cast from solution. The recesses are filled to the appropriate depth and the solvent removed. The hydrophilic foam material which is to comprise the polymeric foam, is then cast on top of the polymeric material. When the polymeric foam has set, the sheet material is removed from the thus formed dressing. If a dressing is required which has zones on both the first and second surface of the foam layer then an additional sheet having polymeric material filled recesses placed so that it opposes the first sheet before the foam comprising the polymeric foam layer has completely set, thereby providing a dressing with zones on both the first and second surfaces. The abovedescribed process is particularly apt for zones which are projections.

A particularly apt process for forming dressings with islands is printing, for example the process often known as transfer printing or screen printing (such as silk-screen printing). Screen printing is particularly suitable. The polymeric material is dissolved in a suitable solvent, spread on a raised template and printed onto the first surface of the foam layer. Where a dressing having zones on both surfaces of the foam layer is desired, this is easily obtained by adding a final step of screen-printing the polymeric material onto the second surface.

Suitable casting solutions for the hydrophilic polymer foam can contain from 15% to 35% by weight of, for example a thermoplastic polyurethane and preferably contain 20% to 30% by weight ESTANE 5714F in tetrahydrofuran or mixtures of tetrahydrofuran, and acetone.

Suitable surfactants for use in making hydrophilic polymer foams include non-ionic surfactants. Favoured non-ionic surfactants are oxypropylene-oxyethylene block copolymers known as Pluronics marketed by BASF Wyandotte. Another favoured non-ionic surfactant is a polyoxyethylene stearyl ether known as Brij 72 marketed by Honeywell Atlas.

Composition and processes for making suitable hydrophilic polymer foams is described in for example United Kingdom Application No.2093702 which is incorporated herein by cross-reference.

In a further aspect therefore the present invention provides a method of dressing a wound on an animal body comprising placing over the wound a dressing comprising a conformable hydrophilic polymeric layer having a first surface and an opposed second surface, the first surface having a plurality of discrete zones of a polymeric material, the swellability on contact with water of the polymeric material being less than that of the polymeric foam.

The preferred dressings of the present invention will be described with reference to the accompanying drawings in which FIG. 1 shows a cross-section through a dressing in which the first surface has a plurality of discrete zones of a polymeric material.

Figure 1:
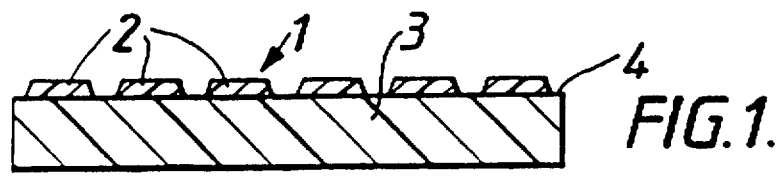

FIG. 1 shows a cross-section through a dressing (1) having discrete zones (2) on a first surface of the foam layer (3). The discrete zones are in the form of truncated-square pyramids. The zones are separated to leave surfaces of the foam uncovered.

Figure 2:
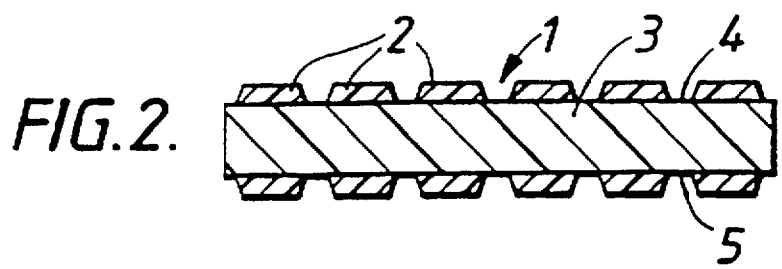
FIG. 2 shows a cross-section through a dressing in which both the first and second surfaces of the polymeric foam layer have discrete zones of a polymeric material.

FIG. 2 shows a cross-section through a dressing which has zones on the first and second surfaces (4 & 5) respectively. The zones need not be arranged to be opposite each other as illustrated.

Figure 3:
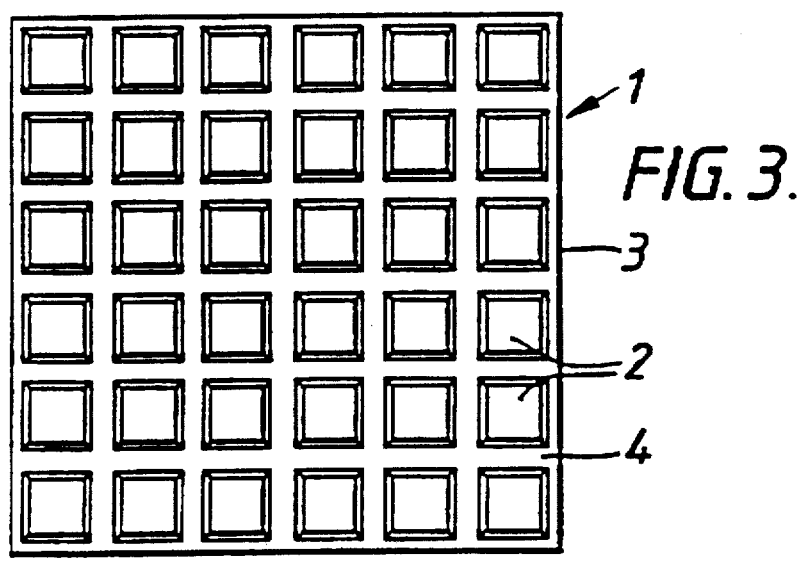
FIG. 3 shows a view from above of a face of a dressing prior to absorption.

FIG. 3 shows a view of the first surface (4) of a dressing prior to any absorption taking place. The zones are separated by a small distance.

Figure 4:
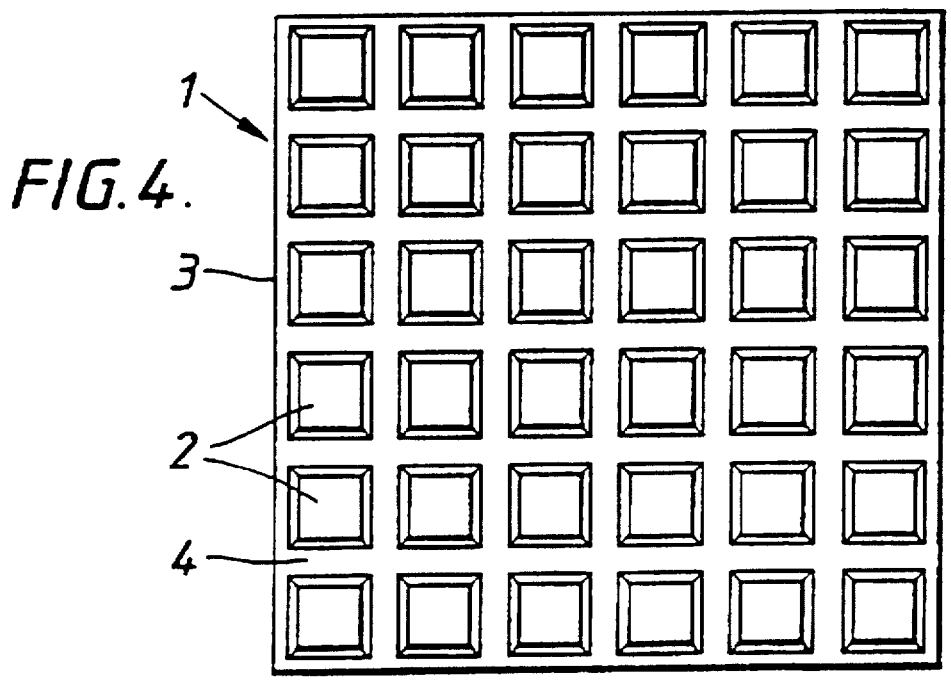
FIG. 4 shows a similar view to FIG. 3 after absorption of an amount of liquid.

FIG. 4 shows the dressing of FIG. 3 after absorption of fluid. The zones have moved apart in two directions in the plane of the surface of the foam.

Figure 5:
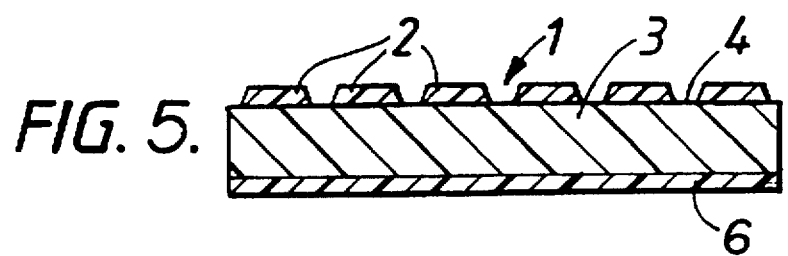
FIG. 5 shows a cross-section through a modification of the dressing of FIG. 1.

FIG. 5 shows a cross section through a dressing like that of FIG. 1 further including a moisture vapor permeable layer 6 on a second surface of the foam layer 3.

Analogous effects are seen when the zones in the dressings are the lower islands.

EXAMPLE 1

A solution containing 20% by weight of a polyether polyurethane (ESTANE 5714F, Trade Mark) in 60/40 (weight by weight) mixture of tetrahydrofuran/acetone was cast in to the recesses of a 15 cm wide silicone sheet in which the recesses were in the form of truncated square pyramids. The recesses were filled sufficiently to provide individual truncated pyramids on the bottom of each recess approximately 60 μm thick after removal of the solvent by drying in a hot air oven.

The hydrophilic foam was cast on top of the polyurethane truncated pyramids by using a two component dispensing unit (Vario-mix supplied by Prodef Engineering Ltd), a foaming mixture was formed by mixing Hypol FHP 2002 and Brij 72 (2% aqueous solution) in a ratio of 1:2.25. The foaming mixture was fed into the coating head by means of an output nozzle in the form of a 15 cm fish tail die and coated by means of a knife over a roller-coating head. The cast foam was dried by passage through an air circulating oven at a temperature of 50° C. for 5 minutes. The resultant dressing material in the form of a strip of foam in which one surface has discrete projections was then removed from the silicone recessed sheet.

The material may be cut to the appropriate size, packaged within a conventional bacteria proof pack and sterilised. In use the dressing is removed from the pack and placed with the projections against the wound area.

EXAMPLE 2

Two similar strips of dressing material were prepared as described in Example 1 except that before the foam had set, the two strips were brought together under slight pressure foam side against foam side so that the foam surfaces adhered to each other and a dressing strip resulted, in which there were projections on both surfaces of the dressing.

The effectiveness of the dressing prepared in Example 1 to expand and contract was observed by placing colored water on to the surface of the dressing possessing the projections. The water was observed to be rapidly absorbed into the hydrophilic foam and the projections to move apart by over 100% of their starting distance apart. On allowing the water to dry from the dressing the projections returned to their original positions.

EXAMPLE 3

A solution of polyurethane (ESTANE 5702) (35% in methyl ethyl ketone) was coated on to a base film (175 µm thick polypropylene) in which square raised areas (3 mm×3 mm) were separated by depressed areas 1 mm thick. This coating was transferred to the surface of a foam in its hydrated (expanded) form. The foam was dried at ambient temperature. The resulting dressing comprised a layer of foam about 2 mm thick, having discrete square areas of polyurethane film about 10 µm thick on the first surface thereof.

When the dressing was placed on a wet surface the dressing absorbed moisture and expanded allowing more moisture to be absorbed and transmitted through the foam layer. When the wet surface dried to the point where only a small amount of residual moisture remained, the foam dried, the projections moved back towards each other and the surface retained some moisture.

EXAMPLE 4

A dressing analogous to that of Example 3 was prepared except that both the first and second surface of the foam have discrete zones having square-shaped surface areas of polyurethane film about 10 µm thick.

According to the present invention, there is provided a further method of manufacturing the dressing in which the foam layer is cast to the desired thickness; and thereafter a polymeric material is dispersed onto a first surface of the foam layer to form a plurality of discrete zones on the first surface.

What is claimed is:

1. An absorbent wound dressing comprising a conformable absorbent hydrophilic polymeric foam layer having a first surface and an opposed second surface, the first surface having thereon wound-contacting polymeric material, and the second surface permitting the passage of moisture vapor, said polymeric material being present on said first surface in the form of a plurality of discrete zones of said polymeric material, the swellability on contact with water of the polymeric material being less than that of the polymeric foam such that when the dressing is placed with the zones of polymeric material in contact with a wet wound surface, the zones move apart as the foam layer absorbs fluid from the wet wound and swells, said second surface permitting fluid absorbed by the foam layer to escape from said foam layer as moisture vapor across said second surface.

2. A wound dressing according to claim 1 wherein the second surface of said foam layer has a plurality of discrete zones of said polymeric material, the swellability on contact with water of the polymeric material of said second surface being less than that of the polymeric foam.

3. A wound dressing as claimed in claim 1 wherein the second surface of said foam layer is covered by a moisture vapor permeable film.

4. A wound dressing as claimed in claim 3 further comprising an adhesive layer which adheres the moisture vapor permeable film to the second surface of the foam layer.

5. A wound dressing as claimed in claim 3 wherein the moisture vapor permeable film extends beyond the foam layer.

6. A wound dressing as claimed in claim 1 wherein said polymeric foam comprises an open cell polymeric foam.

7. A wound dressing according to claim 2, 3 or 6, wherein the polymeric foam comprises a synthetic polymer.

8. A wound dressing according to claim 2, 3 or 6, wherein the polymeric material comprises a synthetic polymer.

9. A wound dressing according to claim 2, 3 or 6, wherein the polymeric material comprises a natural polymer.

10. A wound dressing as claimed in claim 2, 3 or 6, wherein the polymeric foam comprises a polyurethane.

11. A wound dressing as claimed in claim 2, 3 or 6, wherein the polymeric material comprises a pressure sensitive adhesive.

12. A wound dressing as claimed in claim 2, 3 or 6, wherein the polymeric material comprises a polyether polyurethane.

13. A wound dressing as claimed in claim 2, 3 or 6, wherein the polymeric material comprises a polyester polyurethane.

14. A wound dressing as claimed in claim 2, 3 or 6, wherein the polymeric material comprises an elastomeric synthetic polymer.

15. A wound dressing as claimed in claim 1 wherein said polymeric foam consists essentially of an open cell polymeric foam.

16. In a method of treating a wound which comprises applying an absorbent wound dressing to a wound, the improvement wherein the absorbent wound dressing comprises a conformable absorbent hydrophilic polymeric foam layer having a first surface and an opposed second surface, said second surface permitting the passage of moisture vapor, and said first surface having thereon a wound-contacting polymeric material, said polymeric material being present on said first surface in the form of a plurality of discrete zones of said polymeric material, the swellability on contact with water of the polymeric material being less than that of the polymeric foam, such that when the dressing is placed with the zones of polymeric material in contact with a wet wound surface, the zones move apart as the foam layer absorbs fluid from the wet wound and swells, and permitting fluid absorbed by the foam layer to escape from said foam layer as moisture vapor across said second surface.

17. A method of manufacturing an absorbent wound dressing comprising a conformable absorbent hydrophilic polymeric foam layer having a first, wound facing, surface and an opposed second surface permitting the passage of moisture vapor, the first surface having a plurality of discrete zones of a wound-contacting polymeric material, the swellability on contact with water of the polymeric material being less than that of the polymeric foam such that when the dressing is placed with the zones of polymeric material in contact with a wet wound surface, the zones move apart as the foam layer absorbs fluid from the wet wound and swells, said second surface permitting fluid absorbed by the foam layer to escape from said foam layer as moisture vapor across said second surface, said method comprising casting the foam layer to the desired thickness, and thereafter dispersing said polymeric material onto said first surface of the foam layer to form said plurality of discrete zones on the first surface.

18. A method of manufacturing an absorbent wound dressing comprising a conformable absorbent hydrophilic polymeric foam layer having a first surface and an opposed second surface permitting the passage of moisture vapor, the first surface having a plurality of discrete zones of a wound-contacting polymeric material, the swellability on contact with water of the polymeric material being less than that of the polymeric foam such that when the dressing is placed with the zones of polymeric material in contact with a wet wound surface, the zones move apart as the foam layer absorbs fluid from the wet wound and swells, said second surface permitting fluid absorbed by the foam layer to escape from said foam layer as moisture vapor across said second surface, said method comprising casting a plurality of discrete zones of said polymeric material into a mould and casting said foam layer to a desired thickness onto the polymeric material.

* * * * *